United States Patent [19]

Lefebvre

[11] Patent Number: 4,717,425
[45] Date of Patent: Jan. 5, 1988

[54] IMMOBILIZED INORGANIC DIFFUSION BARRIERS AND THE USE THEREOF IN THE SEPARATION OF SMALL MOLECULAR SPECIES FROM A SOLUTION

[75] Inventor: Michel S. M. Lefebvre, Sydney, Australia

[73] Assignee: Limitinstant Limited, London, United Kingdom

[21] Appl. No.: 552,035

[22] PCT Filed: Feb. 22, 1983

[86] PCT No.: PCT/AU83/00023
§ 371 Date: Oct. 12, 1983
§ 102(e) Date: Oct. 12, 1983

[87] PCT Pub. No.: WO83/02905
PCT Pub. Date: Sep. 1, 1983

[30] Foreign Application Priority Data

Feb. 26, 1982 [AU] Australia .................... PF2870
Feb. 26, 1982 [AU] Australia .................... PF2895
Feb. 26, 1982 [AU] Australia .................... 87532/82

[51] Int. Cl.[4] .................... C13D 3/16; B01D 13/01
[52] U.S. Cl. .................... 127/10; 127/46.1; 127/54; 127/55; 210/263; 210/295; 210/500.23; 210/644; 210/651; 210/660; 210/321.79
[58] Field of Search ............... 127/9, 10, 29, 30, 46.1, 127/46.3, 49, 54, 55; 210/649, 660, 651, 650, 195.2, 253, 255, 259, 263, 321.2, 500.23, 644, 295, 433.2

[56] References Cited

U.S. PATENT DOCUMENTS 2,361,000 10/1944 Zender .................... 210/321.1 X
2,593,540 4/1952 Cornwell et al. .......... 127/54 X
2,688,572 9/1954 Warshaw ................. 127/54
3,497,394 2/1970 Berger ................... 210/638
3,799,806 3/1974 Madsen .................. 127/54
3,846,236 11/1974 Updike .
3,867,285 2/1975 Keller, Jr. ............. 210/671
3,926,799 12/1975 Thomas et al. .

(List continued on next page.)

FOREIGN PATENT DOCUMENTS 408042 4/1968 Australia .
414729 10/1968 Australia .
512306 1/1979 Australia .
6980781 11/1981 Australia .

(List continued on next page.)

OTHER PUBLICATIONS

S. Glasstone, "Textbook of Physical Chemistry", 2nd Ed, 1963, Macmillan & Co. Ltd., pp. 651–655.

Primary Examiner—Richard V. Fisher
Assistant Examiner—W. Gary Jones

[57] ABSTRACT

The modification of a diffusion barrier by the deposition of one or more inorganic species within the pores and on to the surfaces of said diffusion barrier to form an immobilized crystalline lattice barrier or molecular grid having substantially uniform permeability and to select and separate different ionic species, giving a high efficiency of separation with a low energy input. The diffusion barrier is characterized by one or more units, each incorporating a tubular housing with a bundle of porous hollow fibres therein, arranged in the axial direction of the housing. The inorganic crystalline lattice is exemplified by barium sulphate ($BaSO_4$) formed by the interdiffusion of barium hydroxide ($Ba(OH)_2$) and sulphuric acid ($H_2SO_4$) solutions, or, alternatively, co-precipitated aluminium hydroxide ($Al(OH)_2$) and barium sulphate ($BaSO_4$) formed by the interdiffusion of barium hydroxide ($Ba(OH)_2$) and aluminum sulphate ($Al_2(SO_4)_3$) solutions. These immobilized inorganic diffusion barriers are used for selective separation of small molecules (e.g. with a molecular weight of less than 1000 daltons) and provide means for the more effective separation of ionic species. A method is also provided for the low cost removal of ions from molasses, to enhance fermentation efficiency and to improve its usefulness as a stock feed supplement, or it may be followed by other treatments to reduce and/or remove higher molecular weight substances, such as proteins and waxes, to produce sugar syrups and caramel substitutes.

40 Claims, 2 Drawing Figures

U.S. PATENT DOCUMENTS

| | | |
|---|---|---|
| 3,956,112 | 5/1976 | Lee et al. ............................ 210/644 |
| 3,996,141 | 12/1976 | Updike . |
| 4,069,157 | 1/1978 | Hoover et al. . |
| 4,188,418 | 2/1980 | Livingston . |
| 4,196,070 | 4/1980 | Chao et al. ..................... 204/252 X |
| 4,214,020 | 7/1980 | Ward et al. ..................... 210/490 X |

FOREIGN PATENT DOCUMENTS

| | | |
|---|---|---|
| 0039179 | 4/1981 | European Pat. Off. . |
| 0040282 | 11/1981 | European Pat. Off. . |
| 2537389 | 2/1977 | Fed. Rep. of Germany . |
| 2750897 | 5/1979 | Fed. Rep. of Germany . |
| 406843 | 12/1909 | France . |
| 877468 | 9/1942 | France . |
| 886705 | 7/1943 | France . |
| 1384557 | 11/1964 | France . |
| 54-002276 | 9/1979 | Japan . |
| 179919 | 7/1923 | United Kingdom . |
| 430426 | 6/1935 | United Kingdom . |
| 506889 | 6/1939 | United Kingdom . |
| 1037879 | 8/1966 | United Kingdom . |
| 1228825 | 4/1971 | United Kingdom . |
| 1336702 | 11/1973 | United Kingdom . |
| 1361674 | 7/1974 | United Kingdom . |
| 1480018 | 7/1977 | United Kingdom . |
| 1509392 | 5/1978 | United Kingdom . |
| 1524429 | 9/1978 | United Kingdom . |
| 1534359 | 12/1978 | United Kingdom . |
| 2010121 | 6/1979 | United Kingdom . |
| 2015368 | 9/1979 | United Kingdom . |
| 1581194 | 12/1980 | United Kingdom . |
| 2054644 | 2/1981 | United Kingdom . |

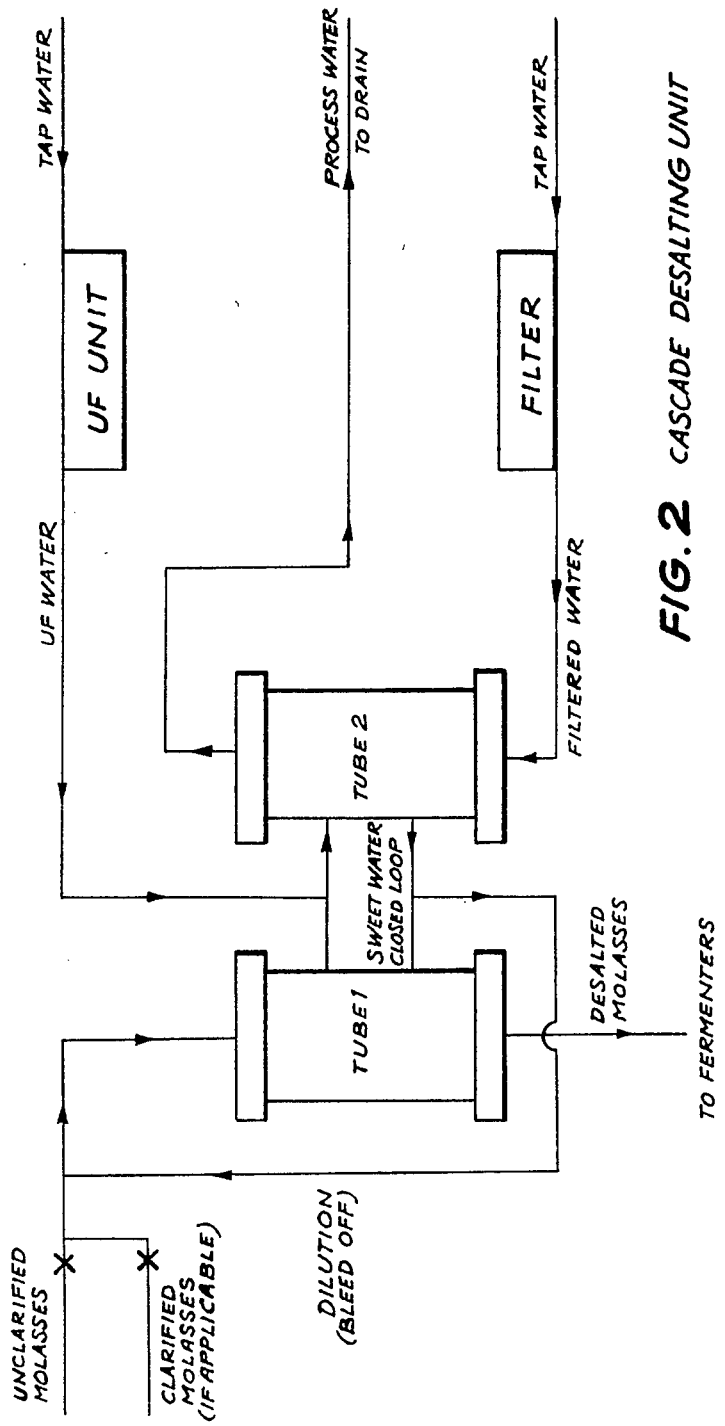
FIG. 2 CASCADE DESALTING UNIT

IMMOBILIZED INORGANIC DIFFUSION BARRIERS AND THE USE THEREOF IN THE SEPARATION OF SMALL MOLECULAR SPECIES FROM A SOLUTION

CROSS REFERENCE TO RELATED APPLICATION(S)

This United States application stems from PCT International Application No. PCT/AU/83/00023 filed Feb. 2, 1983.

TECHNICAL FIELD

The present invention relates to the modification of diffusion barriers by the immobilization of inorganic species therein to increase the selectivity of the barrier, and to the use of such barriers in the separation of small molecularspecies from a solution.

BACKGROUND ART

Various types of membrane diffusion barriers are known according to the published prior art. Molecular and ionic species diffuse through such membranes according to the value of their diffusion coefficient, and for that reason their selectivity is generally poor. Also known according to the prior art are liquid membranes, immobilized liquid membranes or interfacial polymerization membranes which, whilst useful in certain specific applications, suffer the same defects as other previously known membranes.

Small molecular weight separations are not easily achieved by economical industrial stage processes. Classical hyperfiltration requires high pressure and high-equipment cost for the low selectivity, low fluxes and the always present risk of membrane fouling. Chromatography, including high pressure liquid chromatography, gives excellent selectivity but is limited to laboratory scale separations, and is a too costly operation for most industrial applications. Ion exchange, ionic exclusion, transport depletion and reverse electrodialysis are processes applicable only when macro-molecules, with isoelectric points different to the overall pH, are not present in large quantities, otherwise poisoning occurs. Furthermore, high investment cost and high operating cost prohibits their use for the treatment of cheap feedstocks for the fermentation industry.

DISCLOSURE OF THE INVENTION

It is an object of this invention to provide a diffusion barrier for a fluid medium (gas or liquid) with a porosity greater than about 10-20% for channel dimensions of the order of only several Angstrom.

It is also an object of this invention to provide a selective diffusion barrier wherein a predetermined inorganic species is immobilized within the matrix thereof, to produce a diffusion barrier having a substantially uniform molecular grid structure which functions as an effective molecular screen for the selective separation of small molecules (e.g. molecular weight less than about 1,000 daltons) and provides means for the more effective separation of ionic species. The matrix used can be any known diffusion barrier e.g., sintered glass, dialysis membranes, porous metals, or any other suitable porous structure.

It is another object of the present invention to utilize existing diffusion barriers as a support to undergo chemical reaction to manufacture a substantially uniform grid of precise molecular size, with regard to the molecular size of the species to be separated.

It is an object of the present invention to provide a substitute for ion exchange; to provide a method of separating ionic species and non-charged species from an organic media wherein said method has the same effect as direct ion exchange treatment but which avoids the disadvantage of poisoning of the ion exchange resin.

It is a further object of this invention to provide a method of, and means for, the separation of small ionic or molecular species from a liquid and for fractionation of said liquid by the use of a diffusion barrier having a uniform pore or molecular grid structure or uniform permeability, wherein the diffusion of small ionic or molecular species is obtained against the osmotic current through said molecular grid structure to achieve a selectivity greater than the ratio of the relative diffusion coefficient of the separated species. As used herein, the phrase "against the osmotic current" is meant to signify the fact that in the presently claimed processes small molecular species (solutes) diffuse through the counter diffusion barrier from the side higher in solute concentration to the side lower in solute concentration, whereas in a conventional osmotic process a solvent or liquid will pass through the diffusion barrier from the side lower in solute concentration to the side higher in solute concentration.

It is another object of this invention to provide a method of using unitary separative units to increase the original separation factor of such units by use of a cascade system; to provide a method of increasing the separation factor between two components in a liquid phase which are required to be separated, without using the multi-stage recycling of classical cascade systems.

It is yet a further object of this invention to provide a method for the desalting of molasses to upgrade the value thereof and to provide the basis for improved sugar recovery therefrom or for the production of a liquid sugar product or a product equivalent to high test molasses. It is also an object to provide an improved feedstock for fermentation which increases the rate of fermentation, the yield of alcohol or other products and the solids concentration of the effluent.

These and other objects of the invention will be further discussed in the following description of the invention.

According to one aspect of the present invention there is provided a method of immobilization of an inorganic material inside a diffusion barrier in the form of a colloidal-, crystalline-, semicrystalline- species, or a mixture thereof, with control of the physical structure of the immobilized species, and without plugging of the outside surfaces of the diffusion barrier. A diffusion barrier so treated, in most cases would not normally lose any more than about 10% of its original permeability.

According to another aspect of the invention there is provided a process for the separation of small molecular species from a primary liquid (e.g. molasses or molasses fermentation dunder) containing one or a plurality of dissolved molecular species of different molecular weight, comprising subjecting said primary liquid to treatment with a diffusion barrier having substantially uniform matrix permeability which separates the primary liquid from a solvent (e.g. water), wherein an osmotic gradient exists between the primary liquid and the solvent, and whereby small molecular species, especially salts, are selectively transferred from the primary liquid to the solvent against the osmotic current.

The diffusion of the small molecular species against the osmotic current provides a selectivity greater than the ratio of the relative diffusion coefficient of the separated species.

Although the diffusion barrier to be used may be any suitable porous diffusion medium having uniform permeability to enhance the selectivity of the separative process, the preferred diffusion barrier comprises hollow fibres contained in a hollow fibre tube unit having substantially uniform permeability, wherein the primary liquid is circulated through the inner channels or lumens of a bundle of hollow fibres and wherein the solvent is circulated in the space surrounding the bundle of hollow fibres, whereby the small molecular species can diffuse through the molecular screen provided by the uniform grid structure in the walls of the hollow fibres against the osmotic current and into the solvent.

In another aspect of the present invention the solvent circulating in the space surrounding the bundle of fibres is further treated in a cascade system to separate the molecular species contained therein. Preferably the solvent circulating in the space surrounding the bundle of hollow fibres is circulated to the space surrounding the bundle of hollow fibres of a second hollow fibre tube unit wherein an osmotic gradient exists between the solvent in said space and a further solvent circulating through the interior channels or lumens of the hollow fibres of the second hollow fibre tube unit, whereby small molecular species are selectively transferred from the solvent in said space to the further solvent circulating through the interior channels or lumens of the hollow fibres of the second hollow fibre tube unit. The treated solvent from the space surrounding the bundle of hollow fibres of the second hollow fibre tube unit is normally circulated back to the space surrounding the bundle of hollow fibres of the first hollow fibre tube unit. In order to regulate or to control the concentration of dissolved material being recirculated with the solvent in the coupled hollow fibre tube units, a part of the treated solvent from the space surrounding the bundle of hollow fibres of the second hollow fibre tube unit is circulated back to the stream of primary liquid to be treated by the first hollow fibre tube unit. Pure solvent (e.g. water) can be added to the circulating solvent stream to replace the volume of solvent which has been circulated back to the stream of primary liquid (e.g. molasses) to be treated.

It is also within the scope of the invention for the solvent to be further treated by ion exchange or other treatment capable of fixing by adsorption the species to be removed from the solvent.

According to a further aspect of the present invention there is provided a process for the fractionation of a primary liquid (e.g. a sugar-containing solution such as molasses, or dunder from the fermentation of molasses) containing a plurality of dissolved molecular species of different molecular weight, comprising:

(i) subjecting the primary liquid to treatment with a diffusion barrier which separates the primary liquid from a second liquid (e.g. water), wherein an osmotic gradient exists between said primary and second liquids and whereby small molecular species (.e.g. salts) are selectively transferred from the primary liquid to the second liquid against the osmotic current; and (ii) subsequently subjecting said primary liquid to ultrafiltration with a semipermeable membrane, permitting the passage therethrough of water or other solvent component of said primary liquid together with molecules below a predetermined size contained therein (e.g. sugar molecules), to form a permeate of treated product containing said molecules, and preventing the passage of molecules above said predetermined size (i.e. macromolecular species, such as proteins) to form a concentrate or retentate of the remaining components of the primary liquid.

The invention also relates to products—such as molasses or dunder from the fermentation of molasses—which have been treated by the above-described processes and to the fractionated products—such as sugars (in liquid or crystalline form) and protein—obtained as a result of such processes.

In yet another aspect of the present invention there is provided apparatus for the fractionation of a primary liquid containing a plurality, of dissolved molecular species of different molecular weight, comprising:

(i) porous diffusion barrier means with a molecular grid matrix and having substantially uniform grid permeability to enhance selectivity and being adapted to separate said primary liquid from a second liquid whereby small molecular species may diffuse from said primary liquid to said second liquid under the influence of an osmotic gradient between the primary and second liquids; and (ii) ultrafiltration means whereby said primary liquid may subsequently be selectively split into a permeate of a product containing solvent and molecules below a predetermined size, and a concentrate or retentate comprising molecules above said predetermined size.

Ideally, the uniform grid permeability of the diffusion barrier is such that the diffusion of the small molecular species against the osmotic current results in a selectivity greater than the ratio of the relative diffusion coefficient of the separated species.

Preferably, the diffusion barrier means comprises one or more hollow fibre tube units, each comprising a tubular housing; a bundle of porous hollow fibres arranged within the housing in the axial direction thereof; a countercurrent liquid chamber formed between the outer surfaces of the hollow fibre bundle and the inner surface of the housing; first inlet and outlet ports for passing the second liquid into and out of the liquid chamber; partition walls supporting the hollow fibre bundle, separating the open ends of the hollow fibres from the liquid chamber and defining the length of the liquid chamber; and second inlet and outlet ports for the primary liquid phase, the second inlet and outlet ports communicating with the interior space or lumen of each of the hollow fibres, and wherein a plurality of channels of predetermined molecular dimensions and permeability communicate between the interior space or lumen of each hollow fibre and the liquid chamber.

Preferably, in order to provide a system whereby the second liquid circulating in the countercurrent liquid chamber may be treated to remove dissolved ionic or molecular species therefrom, for example as may be required for environmental considerations, a cascade system may be provided wherein the first inlet and outlet ports of each hollow fibre tube unit are connected in series to the first inlet and outlet ports of a second hollow fibre tube unit for circulation of the second liquid therebetween.

In a further modification thereof, an open cascade system is provided wherein means are provided for directing at least part of the treated second liquid back to the stream of primary liquid to be treated by said apparatus, and wherein further means are provided to add pure second liquid (e.g. ultrafiltered water) to replace the treated second liquid which had been removed.

The cascade system contains a solvent for the stripped molecule, which can be different to the solvent used for the primary liquid, and for the outside stripping current of the second unit, provided that if this solvent is different, it is not miscible with the other two solvents.

As a further modification of the invention, ion exchange means and/or other means capable of fixing the dissolved species by adsorption may be provided to remove compounds from the second liquid which have diffused therein from the primary liquid which have diffused therein from the primary liquid. For example, the apparatus may also comprise one or more of the following features.

(i) one or more ion exchange resins to selectively remove the ions or charged molecules required to be stripped, and which can be regenerated by classical ion exchange using a strong base or a strong acid.

(ii) one or more Sirotherm-type units, as developed by the CSIRO, which can strip the current from charged species and which can be regenerated by thermic treatment.

(iii) one or more adsoprtion units e.g., activated carbon, which can be regenerated by thermic treatment.

(iv) one or more metastable ionic systems which can be regenerated by differential pressure.

(v) a solvent inlet, if the solvent used is the same as the base solvent of the primary liquid being treated, to maintain the volume of the closed circuit system constant, and to equilibrate the transfer of solvent due to the difference in osmotic pressure between the inner core and the outer core of the first unit, and in this particular case taking into account the lesser transfer of the same nature occurring in the second unit.

(vi) a unit for selective separation of a two-phase liquid when the closed circuit uses a two-component fluid of non-miscible solvent—as in solvent extraction where one solvent is the solvent used in the primary liquid being treated, whereas the other solvent is a better solvent for the species to be stripped than is the first mentioned solvent.

(vii) a device to make an emulsion of one solvent in another when feature (vi), above, is used.

(viii) a pump to ensure recirculation.

(ix) an outlet from the closed circuit to bleed the product in recirculation back to the original product to be treated.

Classical dialysis processes use membranes, isotropic or anistropic, with pore dimensions small enough to limit water convection by a sufficient amount so as to avoid interference between molecules and their first sphere of hydration, and the wall. Under these circumstances, classicial diffusion laws apply, and dialysis is performed in direct relationship with the respective values of the molecular speices concerned. Pore uniformity, in this case is not crictical and the value of measured diffusion coefficients are in essence the same as the ones measured in sintered glass diffusion cells (this being corrected using the relative value of membrane resistance and interface resistance (see Scheitzer, "Handbook of Separation Techniques", McGrawhil).

However, with a uniform grid of molecular dimensions close to half the mean free path of the respective molecules, selective counter dialysis occurs. This effect is possible only if none of the pores offer free passage to solvent detrimental to the equilibrium water flux/diffusion, or, in other words, if bulk back diffusion is minimal.

In this process, a membrane or other diffusion barrier is interfaced with two fluids: one with high osmotic pressure, the other with low osmotic pressure. Fluid 1 contains various low molecular weight species, to be selectively transferred to Fluid 2. If we consider two molecular weight species (a) and (b) with bulk concentration in Fluid 1 being $C_{1A}$ and $C_{1B}$ transferable through the membrane pores, each species transfers according to their relative concentration gradient and their diffusion coefficient with local transport vectors $D_A$ and $D_B$. A counter current of water inside the pore, corresponds to a local transport vector $D_W$. $D_A$ and $D_B$ are directly related to the thin wall concentration gradient (i.e. $C'_{1A}$, $C'_{1B}$, $C'_{2A}$, $C'_{2B}$ replaced $C_{1A}$, $C_{1B}$, $C_{2A}$, $C_{2B}$ in respective equations). In the same manner $D_W$ depends on the real osmotic pressure difference between the two membrane walls and not the osmotic pressure difference measured from the bulk concentration of the species (due to concentration polarisation). Variation of $C'_{1A}$ versus $C_{1A}$, or more generally $C'$ value versus C values, are governed by the Blatt equation which expresses the influence of shear rate on concentration polarisation. For a given value of $C_{1A}$ it is always possible to choose a value of $D_W$ such as $$|D_B|<|D_W|<|D_A|$$

by adjusting the shear rate values relative to Fluid 1 and Fluid 2 or the pressure gradient across the membrane to selectively modify $D_W$.

However, in practice, the dimensions of the modified pore structure (i.e. from about 50 Angstrom to about 10 Angstrom) are such that phenomena other than classical diffusion have to be taken into account, and the present invention utilises the maximum interaction between the immobilized inorganic species, the ionic species in solution and/or the first or second sphere of hydration.

In this regard, at least four separate phenomena have to be considered as complimentary to classical diffusion:

(i) Anomalous diffusion phenomena. In the example given above $D_A$ and $D_B$ can be influenced by the relative local concentration gradients of the two species, the less mobile ion being slowed down by the most mobile ion—e.g., $K^+$ diffuses faster than $Na^+$; if the concentration of $Na^+$ increases then the rate of diffusion of $K^+$ will increase whilst that of $Na^+$ decreases.

(ii) Donnan equilibrium effect to respective electroneutrality of transfer.

(iii) Ionic species which are associated with water through strong or tight bonds for their first sphere of hydration, are generally associated with a second sphere of hydration through loose or weak bonds, which can be explained only by the partial orientation of the molecule of water or solvent outside of the first sphere or hydration. In this case the second sphere of hydration is defined by a level of energy being the difference between the energy state of the random molecule concerned, and the partly re-entered state. The channel dimensions at the level of the second sphere of hydration are used to selectively influence the diffusion of the species. In this regard, the minute difference between the energy levels involved in the coordination of the solvent molecules inside the second sphere of solvation allows for discrimination between ionic species which have the same outer shell electron structure (e.g. between hafnium and Zirconium).

(iii) Close molecular interactions between wall, solute and solvent. The coordination energy between a wall and an adjacent ionic species can be used to differentiate between ionic species, and this energy is linked to the solubility product of the molecular species obtained by the combination of oppositely charged ions in the wall. For example, if Barium Sulfate is used as the major component of the grid, $SO_4^{2-}$ ions will not diffuse, or will diffuse much slower, because the solubility product $[Ba^{2+}][SO_4^{2-}]$ is extremely small, but $Cl^-$ ions will diffuse without measurable difference compared to the normal diffusion coefficient, because the solubility product $[Ba^{2+}][Cl^-]^2$ is large.

BEST MODE OF CARRYING OUT THE INVENTION

Expressed in another way, a reaction is effected between two reactants, each in the form of a solvent and a solute circulating on opposite sides of a primary matrix. For example, if the matrix is in the form of a hollow fibre th reaction is conducted between two solutions 'A' and 'B', containing solutes 'a' and 'b', respectively, circulating on opposite sides of the hollow fibre matrix, and 'A' on the outside and 'B' on the inside.

The components to be immobilized are insoluble in both solvents a' and b', or at least totally insoluble in one of them.

For immobilization of a predetermined compound 'c', obtained by the reaction between solutes 'a' and 'b' according to the following reaction scheme:

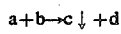

the active ionic parts of 'a' and 'b' each have their stoichiometric proportions determined by the reaction, but corrected by their diffusion coefficient or their ionic mobility.

For example, the immobilization of Barium Sulfate ($BaSO_4$) inside a hollow fibre-type membrane is effected by the reaction between Barium Hydroxide ($Ba(OH)_2$) solution outside the hollow-fibre and Sulfuric Acid solution ($H_2SO_4$) inside the fibre. The rate of reaction is controlled so as to have stoichiometric proportions of $Ba^{2+}$ and $SO_4^{2-}$ inside the membrane at the start of the reaction.

In other words the value of the diffusion coefficient for $SO_4^{2-}$ is used to correct the concentration of $H_2SO_4$ used to have the same ionic concentration as $Ba^{2+}$ at the interface. Expressed in another way, it is not sufficient to simply determine the stoichiometric proportions of the two solutions which are used, as it is also necessary to take into account the different speeds of diffusion. Diffusion coefficients of various ionic species can be found by reference to standard texts. Multiplication of the appropriate diffusion coefficient by the concentration of the ionic species gives the quantity of ions which will be present at a certain time at the interface. With this figure determined it is then necessary to check the quantity of ions of the other species which will be present and to adjust the concentration if necessary such that exactly the same concentration or stoichiometric proportion will be present at the interface, concurrently. In respect of the formation of crystals of inorganic species in the membrane, allowance can be made as far as the diffusion coefficients are concerned by the variation of such diffusion coefficients versus temperature if the temperature of the two streams are not the same.

A slight disequilibrium, with a higher concentration of component 'a', will create immobilization on the side in contact with component 'b'. In other words, in the example given above, if the concentration of $Ba(OH)_2$ which is used is higher than the predetermined concentration, the $Ba(OH)_2$ outside of the hollow fibre will cause the immobilization of $BaSO_4$ on the inner core of the hollow fibre.

In the general reaction sequence given above, any reaction between 'a' and 'b' which produces at least one insoluble product in one of the solvents contained by solutions 'A' and 'B' can be used.

The density of the precipitate will be highest in the layer which is formed initially, but will be gradually lower for subsequently formed layers inside the fibre, extending to the outside side of the hollow fibre.

It is also within the scope of the present invention to immoblize two different layers of inorganic species in and on the diffusion barrier, one inorganice species giving selectivity for one specific component, the other inorganic species given selectivity for one or more other components contained in the solution being treated.

In practice it is normally possible to take any inorganic compound which is not soluble in one of the solvents which is being used. From the chemical formula of this compound it is possible to determine the reaction scheme of sequence which will lead to that compound. With two components in the reaction, the diffusion coefficients are determined for each component, and based on the teachings of the present invention it is possible to determined the requirements to effect immobilization of the compound.

The preferred diffusion barrier is a porous hollow fibre wih a wall thickness of about 3 to about 15 microns and an internal channel height or diameter of about 200 microns.

In an embodiment of the invention relating to the desalting of molasses, the diffusion barrier used was a 1.8 square metre hollow fibre unit, treated such that $Al(OH)_3$ and $BaSO_4$ were immobilized therein as a co-precipitate, obtained by the reaction between $Al_2(SO_4)_3$ and $Ba(OH)_2$. To work out the precise concentrations required the above described technique (determining diffusion coefficients, etc) is followed, with the regeneration of a solution of saturated $Ba(OG)_2$ outside the hollow fibre and $0.158N$ $H_2SO_4$ inside. With this system, typically 500 gm of molasses is diluted with 500 ml of $H_2O$, giving a total volume of 830 ml, and this solution is circulated inside the hollow fibre with a flow rate of 400 ml/minute. Outside the hollow fibre $H_2O$ is circulated at a flow rate of 2 liters/minute.

With such diffusion barriers of the type referred to above, the mechanism for selectivity is of five types:

(1) Selectivity by ionic interaction. When you have an inorganic precipitate as a barrier, the remaining charge influences the flow of molecules by proximity influence, e.g., $BaSO_4$ is selective against $SO_4^-$ but allows $Cl^-$ to pass.

(2) Differential site-to-site transport, e.g., an hydrophobic barrier will selectively transport any agent which can be solvated, especially any plasticizer of such a barrier against water. Site-to-site transport is a step-by-step operation, which includes:
  (i) adsorption of molecules;
  (ii) diffusion through the barrier, and
  (iii) desorption from the barrier to the second layer.

(3) Selectivity by virtue of the osmotic gradient between two liquid phases separated by the barrier. In this case, solvent counter-current opposes the transport of the diffusing species. If the maximum grid dimension is less than the free path of the diffusing molecule, the counter-current effect of solvent makes a selective separation against the apparent surface of resistance offered by the molecule to the flow of solvent transported back.

(4) Anomalous diffusion, as described above.

(5) Selective counter dialysis, as described above.

Unfortunately, these selective modes—and especially those outlined in (2) and (3), above—are not 100% effective. In the case where it is required to make a separation between small ionic species and small non-charged species, it is difficult to obtain a complete separation—and especially to completely block the transport of non-charged species e.g., in the case of the desalting of, or the selective removal of ionic species from, a complex organic media, where it is required to avoid the transport of small organic molecules, such as in the desalting of any sugar syrup (e.g. molasses).

One classical prior art method to achieve such a separation is to use ion exchange resins, which give in two steps the deionization of the complex mixture.

Unfortunately, ion exchange sites prepared in a microporous matrix are very sensitive to poisoning by large organic molecules which are, in most cases, present in the original media. For this reason it is important to avoid any contact between molecules bigger than the inner pore structure of the ion exchange resin, and the resin itself.

The invention will be further described with reference to an embodiment thereof relating to the desalting of cane sugar molasses.

In general terms, molasses contains about 55% sugars by weight (80% by volume), 25% water and approximately equal amounts of salts and large organic molecules. The large molecules (molecular weight above 20,000) are mainly proteins and waxes and the salts primarily comprise K, Mg, Na and Ca ions associated with chlorides and sulphates as counter ions.

The sucrose content in molasses varies between 25 to 40%, and the reducing sugars range from 12 to 35%, but the sum of the two generally constitutes at least 50 to 55% of the final molasses.

However, the accumulation of salts and higher organic molecules in molasses constrains economic sugar recovery therefrom, and reduces its value in fermentation and in the stock food industries.

The high salt content of molasses, especially potassium salts in molasses from sugarcane, has limited its final utilization. The combination of high ash and non-sugars content in molasses limit the recovery of residual sucrose due to complex solubility reactions. In addition the high potash levels in molasses have a laxative effect which limits molasses utilization in animal feeds.

Currently available techniques for salt removal from molasses are based on ion exchange and electrolysis. However, because the high molecular weight components in molasses cause resin and membrane fouling no commercially viable process has been developed for the cane sugar industry.

By means of the use of the present invention it is possible to remove the bulk of the salts (potassium, calcium and magnesium salts in particular) and other small molecules from the molasses to provide treated molasses which is a more useful product for use in more efficient fermentation and for stock food applications.

By subjecting the treated molasses to specific ultrafiltration treatment, it is possible to effectively remove the macromolecular organic compounds (wax, proteins, polycellulosic material) thus creating the conditions for the complete recovery of the sugar content of the molasses, e.g. in the form of a sugar syrup, from which the sucrose can be crystallised, if required. By a combination of hollow-fibre separation and ultrafiltration technology it is possible to deplete the input molasses of a major portion of its salt and large MW species. This yields a sugar syrup of a product equivalent ot treacle or "golden syrup".

According to this embodiment of the invention, the molasses is subjected to an osmotic desalting treatment in a series of hollow-fibre separation units. Preferably, each separation unit comprises a highly selective and highly porous diffusion barrier, with the hollow fibres consisting of regenerated cellulose, being of substantially uniform pore structure and wherein a predetermined inorganic species in the form of a crystalline lattice is immobilized within the hollow-fibre structure, both in the membrane pores and on the surfaces. In this way each hollow-fibre comprises a substantially uniform grid of precise molecular size, with regard to the molecular size of the species to be selected or separated. The type of crystalline lattice can be changed to vary the rejection characteristics of the diffusion barrier.

Molasses is passed through the hollow fibres counter-current to a stream of water (or ultrafiltered water) flowing around the outside of the hollow fibres. Each hollow-fibre unit has an inlet (with pre-filter) and an outlet for the molasses feed and an inlet and an outlet for the counter-current water flow. The pores are such that they will prevent transfer of sugars to the countercurrent water flow, which is further inhibited by the inward flow of water molecules. However, potassium, calcium and magnesium ions are able to move counter to this flow via an ionic diffusion transport mechanism, as described above.

BRIEF DESCRIPTION OF THE DRAWINGS

The embodiment of the invention relating to the desalting of molasses will be further described with reference to the drawings, in which:

FIG. 2 illustrates an open cascade arrangement for the desalting of molasses designed for the recovery of the bulk of any of the sugar content of the molasses which may have bled into the countercurrent water and which is required to be treated before drainage thereof.

Figure 1:
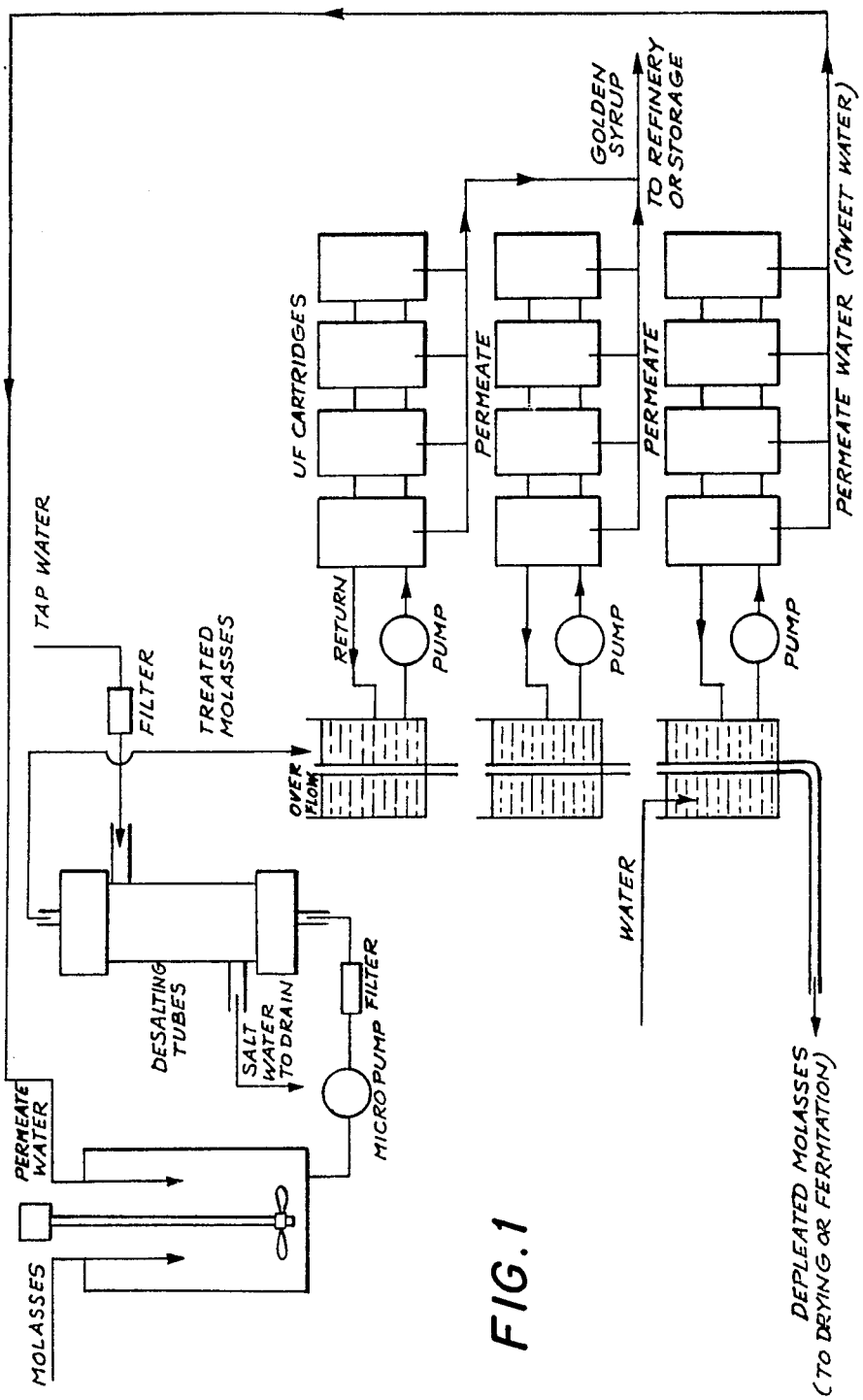
FIG. 1 illustrates a schematic representation of apparatus embodying principles of the present invention and comprising one or more hollow fibre desalting tube units, possibly in one or several banks of such tubes connected in series or in cascade form, depending upon the level of desalting required, and further comprising one or more banks of ultrafiltration units to separate the sugars from the macromolecular components of the molasses, such as proteins and waxes.

Each hollow fibre desalting unit according to the preferred embodiment has an active surface area of 1.8 $m^2$ and comprises a plurality (9,000 to 15,000) hollow fibres with a wall thickness of about 3–15 microns, an internal channel or lumen diameter of about 200 microns. The hollow fibres have a porosity ratio of about 20% with pores or molecular screens of about 10 Angstrom.

As shown in FIG. 1, molasses—diluted with water if necessary—is pumped through the internal channels of the hollow fibres with filtered or ultrafiltered tap water pumped in countercurrent in the space surrounding the hollow fibres. Under the influence of the osmotic gradient which exists, certain ions—including potassium, calcium and magnesium ions—diffuse through the molecular screen provided by the porous wall structure of the hollow fibres, with some water flowing back through the channels and into the molasses stream. According to the flow rate of the molasses pumped through the hollow fibre tubes, and the level of desalting which is required, the molasses may be passed through one or a plurality of banks of such hollow fibre tubes (with tubes in each bank in parallel) to obtain the required level of desalting. For example, the potassium content may be reduced by up to about 90% of the original potassium content, depending upon the number of hollow fibre tube units used and the particular operating conditions applied. More than half of one of the most prolific salts in molasses, potassium, can be removed in a single pass through a bank of hollow fibre tubes. A 60 tube module can produce 1.8 tonnes per hour of substantially desalted molasses while using less than 4 $m^3$ of water per hour with a power consumption of less than 4 KW. Operating pressures are typically less than 50 kpa but depend on the viscosity of the molasses, temperature, flow rate and the desired level of desalting.

Ion levels in the molasses can be determined by atomic absorption spectroscopy before and after passage through the hollow fibre tubes.

The following results have been obtained for a 1.2 $m^2$ membrane using molasses diluted to 520 g/l sugar concentration:

| No. of Passes | Ion Concentrations (g/l) | | | | |
| --- | --- | --- | --- | --- | --- |
| | $K^+$ | $Na^+$ | $Mg^+$ | $Ca^{++}$ | $Cl^-$ |
| Control | 41.4 | 1.1 | 4.6 | 8.4 | 21.3 |
| 1 Pass | 26.0 | 0.72 | 3.2 | 7.0 | 12.4 |
| 2 Pass | 20.0 | 0.60 | 2.5 | 5.0 | 9.5 |
| 3 Pass | 14.0 | 0.49 | 2.0 | 4.6 | 6.8 |

At this stage, if required, the treatment of molasses can be terminated and the desalted molasses returned to the refinery or to the fermentation plant.

However, the desalted molasses may be further treated, in a second phase, by subjecting the desalted molasses to ultrafiltration, to eliminate macro-molecules which have a molecular weight higher than the sugar, i.e. to remove the protein and the wax.

By a combination of hollow-fibre separation and ultrafiltration technology, as shown in FIG. 1, it is possible to deplete the input molasses of a major portion of its salt and large MW species. This yields a sugar syrup or a product equivalent to "Golden Syrup".

The desalted molasses is circulated through a three-stage ultrafiltration system of capillary modules, as shown in FIG. 1. Ultrafiltration effects the separation of different molecular sizes through porous membranes in thin channels at high velocity. Various molecular weight cut-offs are available to adjust the wax and macromolecular content of the molasses to meet market needs and requirements.

The combined effect of the hollow fibre desalting tube and the ultrafiltration equipment permits the removal of the small molecular fraction and the high molecular fraction thus leaving a syrup which contains the sugars (sucrose and invert sugars) and some colouring agents of intermediate molecular weight. This product (treacle of golden syrup) can be either:

Directly used as a liquid sugar substitute and eventually a natural colouring agent (the colour can be adjusted by modification of the molecular weight cut-off of the UF membrane).

Concentrated by multiple effect evaporation to be shipped and used in sensitive fermentation areas (baker's yeast, citric acid, mono sodium glutamate, pharmaceuticals).

Returned to the refinery for sucrose extraction; the low potassium content and the absence of high molecular compounds permits two thirds sucrose recovery per strike.

The equipment is readily tuneable or adaptable to the user's requirements; it is a simple matter to adjust the apparatus to modify the salt content of the product.

Furthermore, the use of different ultrafiltration membranes allows the manufacturer to selectively control the amount of small molecules related to color, taste and surfactant properties for enhancement of colour, taste and eventually mechanical properties of the end product.

The first two stages of the ultrafiltration unit produce the sugar syrup. In the third stage water is added to rinse the molasses. The permeate from Stage III (very dilute syrup "sweet water") is recycled back to the counter-current mixer where it is used to dilute the incoming molasses prior to the desalting stage. Because it is a closed loop system, there is no loss of sugar.

The depleted molasses flow from Stage III is primarily a protein concentrate, containing about 25% protein and wax W/W. For small installations and protein concentrate will simply be discharged to an anaerobic septic tank. For larger installations (e.g. treating in excess of 10,000 tonnes molasses/year) it may be feasible to install a dryer to recover the protein concentrate in powder form. The protein concentrate solution is stable only for about 3 days but when dried it has a stable shelf life of about 12 months.

FIG. 2 of the drawings illustrates an open cascade modification for the hollow fibre tube desalting unit, whether for use as part of the system illustrated in FIG. 1, or for a straight molasses desalting application without the subsequent ultrafiltration treatment.

As shown in FIG. 2, molasses is pumped through the central channels of the hollow fibres of Tube 1 with water pumped at countercurrent in the space surrounding the hollow fibre bundle. To reduce the effect of any sugar bleeding from the molasses into the countercurrent water, said countercurrent water is pumped into the space surrounding the hollow fibre bundle of a second tube (Tube 2) which has been connected to Tube 1. In Tube 2, filtered water is pumped through the central channels of the hollow fibres wherein, under the influence of an osmotic gradient, salts in the water surrounding the hollow fibres diffuse through the porous walls of the hollow fibres and into the water which is circulating through the central channels of the hollow fibres, after which it is passed to the drainage system. The bulk of the sugar which have bled into the water surrounding the hollow fibre bundle of Tube 1 are normally retained in the water circuit between Tubes 1 and 2.

In order to control the level of sugars circulating in the water between Tubes 1 and 2, part of this water is bled off (as shown in FIG. 2) and is recirculated back to the incoming molasses stream where it serves a useful purpose of diluting the feed molasses to an acceptable level of dilution for pumping through the thin channels of the hollow fibres. The sugar-containing water which is bled off is replaced by ultrafiltered water which is feed into the looped circuit between Tubes 1 and 2, as shown in FIG. 2.

In one experimental application molasses containing 50% by weight of sugars and 5% salts was passed through Tube 1. The resulting desalted molasses from Tube 1 contained 49% sugars and 2% salts (i.e. 60% desalting). Consequently, the countercurrent water in Tube 1 contained 3% salts which had diffused through the walls of the hollow fibres from the molasses into the countercurrent water, as well as the 1% of sugars which had bled into the water.

When the countercurrent water was passed into the space surrounding the hollow fibres of Tube 2, and was treated against pure water circulating through the central channels of the hollow fibres of Tube 2, tests indicated that whereas 1.8% of the salts passed into the central channel water, only 0.02% of the sugars bled into this water which was to be directed to drainage.

Thus the water to be recirculated back to Tube 1, or which was to be recirculated back to the incoming stream of molasses, contained the balance of 0.98% of the sugars and 1.2% of the salts. Thus by the open cascade system illustrated in FIG. 2, any loss of sugars by bleeding can be reduced to a minimum, and to an environmentally acceptable level.

The form of the apparatus to be used for the treatment of molasses depends upon the intended end use(s) of the treated molasses and the environmental considerations which must be taken into account at the intended site of operation. Generally, three basic modes of operation are provided.

TYPE 1: Where pollution control is not of primary importance and when the investment has to be minimised, water (preferably ultrafiltered) is fed directly to the outskirt of the tube and molasses to the inner channel (1 kg/mn/tube of molasses for 1.5 l/mn per tube of water). One, two or three passes (one, two or three tubes in series of counter-current) can be used to achieve the necessary level of desalting.

TYPE 2: Where pollution control is important (when the factory is not allowed to reject more than 600 ppm of BOD) a double-tube, open-cascade arrangement, as shown in FIG. 2, is used. This equipment is well adapted to the fermentation industry where a high level of dilution is required.

In this case (Cascade Desalting) the use of UF water is limited to the level of dilution needed for fermentation and the desalting water is simply filtered.

TYPE 3: Where pollution control is paramount (when the factory is not allowed any reject in the form of BOD) water consumption has to be minimal and the dilution of the molasses has to be minimised (for example, for further crystallisation of sugar) an ion exchange resin unit replaces tube number two in the cascade arrangement illustrated in FIG. 2.

For each type the following parameters can be defined:

Desalting level expressed in potassium reduction in % (K%)
Sugar Loss expressed in (invert Equivalent) % (S%)
Separation factor = K%/S%

|  | TYPE 1 | TYPE 2 | TYPE 3 |
| --- | --- | --- | --- |
| Maximum Desalting | 95% | 50% | 99% |
| Separation Factor | 2 steps (6–10) | (30–80) | 1 step (complete separation) |
| Sugar loss per step (as invert) | 3%–5% | 0.2%–1% | 0 |
| UF water per kg of molasses | 1.5 | 0.3–3* | 0.3** |
| Filtered water | — | 1.5 |  |

*according to dilution
**volume in liters
Potassium - reduced 2-3 fold
Sodium - reduced 2-3 fold
Calcium - reduced 4 fold
Magnesium - reduced 2-3 fold
Iron - not affected
Copper - not affected
Molybdenum - not affected In the case of a manufacturer fermenting molasses to produce alcohol, the step of desalting molasses makes his fermentation more efficient in the following ways:

(i) Increased reactivity:

Lower potassium and chlorine levels, results in shorter fermentation times. As this is the most time-consuming operation, and the step requiring the largest capital invention, the manufacturer now has the capability to treat more molasses in any given period. For example, using *Zymomonas mobilis* as the micro-organism for fermentation of a 9% sugar concentration, the following fermentation times were obtained for the same level of sugar transformation:

(a) untreated—34 hours
(b) 1 pass desalting—9.5 hours

Similarly, using the yeast *Saccharomyces uvarum* as the micro-organism, fermentation time was reduced from 32 hours (for untreated molasses) to about 16 hours (using desalted molasses). The actual increase in fermentation capacity a fermenter can obtain by using the desalting process will depend on such factors as the type of molasses used, the sugar concentration and the type of fermentation micro-organism used.

(ii) Increased Yield:

It is possible to transform more sugar to alcohol from each batch of molasses. This means that a manufacturer can produce more alcohol from a given quantity of molasses. Increased Alcohol Level in the 'Beer':

A most important advantage is that at equilibrium (or even before) the level of alcohol that can be produced in the substrate is higher than the amount of alcohol that can be produced in non-treated molasses. This given three advantages:

(a) Increased Productivity—more alcohol produced per batch
(b) Reduced Energy Requirement—distillation of the alcohol requires less energy because there is more alcohol and less water in the beer.
(c) Increased capacity—the reflux of the column can be increased.

The increased efficiency of fermentation, using B.D.C. yeast, significant reduction in the time to reach equilibrium following molasses desalting is shown in the table below:

| | Rate of Alcohol Production | Fermentation Efficiency (hm EtOh/L/Hr) % | Max. EtOh Concentration After 16 h (% V/V) |
|---|---|---|---|
| Non-clarified molasses | 2.0 | 78 | 4.5 |
| Clarified molasses (same installation) | 2.4 | 80 | 5 |
| Clarified molasses | 2.4 | 80 | — |
| Clarified and desalted molasses | 4.1 | 88 | 8.2 |

Another application of the present invention is the immobilization of mineral crystals with total selectivity against NaCl. In other words to have a membrane which is impermeable to NaCl, but which substantially maintains its water permeability; as indicated above, it is a feature of barriers created by the process of the present invention that they do not lose more than about 10% of their original permeability.

Such membranes could find potential use in, for example, concentration of fruit juices (e.g. osmotic pressure about 5 atmospheres) in a run against sea water (osmotic pressure about 35 atmospheres), at absolute minimal energy cost.

The invention further envisages the immobilization of crystals in diffusion barriers in dry form for use as gas permeation barriers. The inventive process of the present invention enables the formation of diffusion barriers with a sufficiently well distributed lattice structure to provide selectivity between gases. Possible applications for such barriers could be the separation of oxygen from the air, the extraction of helium, the purification of gases such as carbonic gas, etc.

Although the invention has been described above with reference to specific examples and preferred embodiments, it will be appreciated that the invention is not limited thereby, and that variations are possible without departing from the spirit or scope of the invention as broadly described.

I claim:

1. A diffusion barrier for selective counter diffusion, comprising a microporous matrix including a plurality of porous hollow fibre membranes and having one or more inorganic salts in the pores and on the inside surfaces of the cores of the hollow fibre membranes and forming an immobilized inorganic molecular grid or screen having a substantially uniform lattice structure defining pores or channels through the fiber walls having a diameter in the range of about 10 to about 50 Angstroms, said diffusion barrier having substantially uniform permeability.

2. The diffusion barrier of claim 1, wherein the immobilized inorganic molecular grid comprises a co-precipitate of two separate inorganic materials.

3. The diffusion barrier of claim 2, wherein the immobilized inorganic molecular grid comprises co-crystals of barium sulphate and an aluminium compound.

4. The diffusion barrier of claim 3, including a protective coating on the immobilized inorganic molecular grid.

5. The diffusion barrier of claim 1, wherein the immobilized inorganic molecular grid comprises a composite layer of different organic materials deposited sequentially onto and within said permeable matrix.

6. The diffusion barrier of claim 5, wherein the immobilized inorganic molecular grid comprises barium sulphate.

7. A process for the fractionation of a primary liquid containing a plurality of dissolved molecular species of different molecular weights, comprising:
(i) subjecting the primary liquid to a selective counter diffusion treatment with a diffusion barrier which separates the primary liquid from a second liquid, said diffusion barrier comprises a microporous matrix having one or more insoluble inorganic salts in the pores of the matrix and forming an immobilized inorganic molecular grid or screen having a substantially uniform lattice structure defining pores or channels therethrough in the range of from about 10 Angstroms to about 50 Angstroms in diameter and substantially uniform matrix permeability, said primary liquid and said secondary liquid being selected such that an osmotic gradient exists between said primary and second liquids and an osmotic current flows through said barrier from said second liquid towards said primary liquid and including the step of controlling at least one of the shear rate of the primary liquid along one side of said diffusion barrier and the osmotic gradient across said diffusion barrier such that small molecular species are selectively transferred from the primary liquid through said diffusion barrier against the osmotic current with a selectivity greater than the ratio of the relative diffusion coefficients of the separated species; and
(ii) subsequently subjecting said primary liquid to ultrafiltration with a semipermeable membrane, permitting the passage therethrough of the solvent component of said primary liquid together with molecules below a predetermined size contained therein, to form a permeate of treated product, and
preventing the passage of molecules above said predetermined size to form a concentrate or retentate of the remaining components of the primary liquid.

8. A process for the separation of small molecular species from a sugar-containing solution, which comprises subjecting said solution to a selective counter diffusion treatment with a diffusion barrier which separates the solution from a solvent, said diffusion barrier comprises a microporous matrix having one or more insoluble inorganic salts in the pores of the matrix and forming an immobilized inorganic molecular grid or screen having a substantially uniform lattice structure defining pores or channels therethrough in the range of from about 10 Angstroms to about 50 Angstroms in diameter and substantially uniform matrix permeability, said solvent and said solution being such that an osmotic gradient exists between the solution and the solvent, and an osmotic current flows through said barrier from said solvent towards said solution and including the step of controlling at least one of the shear rate of the solution along one side of the diffusion barrier and the osmotic gradient across the diffusion barrier such that small molecular species, including salts, are selectively transferred from the solution to the solvent against the osmotic current with a selectivity greater than the ratio of the relative diffusion coefficient of the separated species.

9. The process according to claim 8, wherein the diffusion barrier comprises a hollow fibre tube unit, wherein the solution is circulated through the inner channels or lumens of a bundle of hollow fibres and wherein the solvent is circulated in the space surrounding the bundle of hollow fibres, whereby the small molecular species can diffuse through the uniform molecular grid matrix structure in the walls of the hollow fibres against the osmotic current and into the solvent.

10. A process according to claim 9, wherein the solvent circulating in the space surrounding the bundle of hollow fibres is further treated in a cascade system to separate the molecular species contained therein.

11. The process according to claim 10, wherein the solvent circulating in the space surrounding the bundle of hollow fibres is circulated to the space surrounding the bundle of hollow fibres of a second counter diffusion hollow fibre tube unit wherein an osmotic gradient exists between the solvent in said space and a further solvent circulating through the interior channels or lumens of the hollow fibres of said second hollow fibre tube unit.

12. The process according to claim 11, wherein the treated solvent from the space surrounding the bundle of hollow fibres of said second hollow fibre tube unit is circulated back to the space surrounding the bundle of hollow fibres of the first hollow fibre tube unit.

13. The process according to claim 12, wherein a part of the treated solvent from the space surrounding the bundle of hollow fibres of said second hollow fibre tube unit is circulated back to the stream of sugar-containing solution to be treated by the first hollow fibre tube unit.

14. The process according to claim 13, wherein pure solvent is added to the circulating solvent stream to replace the volume of solvent which has been circulated back to the stream of sugar-containing solution to be treated.

15. The process according to claim 9, wherein the solvent circulating in the space surrounding the bundle of hollow fibres is subjected to ion exchange or other treatment capable of fixing by adsorption the species to be removed from the solvent.

16. The process of claim 15 wherein the sugar-containing solution is selected from the group consisting of, molasses and dunder from the fermentation of molasses.

17. A process for the fractionation of a sugar-containing solution which comprises:
(i) subjecting said solution to a selective counter diffusion treatment with a diffusion barrier which separates the solution from a solvent, said diffusion barrier comprising a microporous matrix having one or more insoluble inorganic salts in the pores of the matrix and forming an immobilized inorganic molecular grid or screen having a substantially uniform lattice structure defining pores or channels therethrough in the range of from about 10 Angstroms to about 50 Angstroms in diameter and substantially uniform matrix permeability, said solution and said solvent being such that an osmotic gradient exits between the solution and the solvent, and an osmotic current flows through said barrier from said solvent towards said solution, and including the step of controlling at least one of the shear rate of the solution along one side of the diffusion barrier and the osmotic gradient across said barrier such that small molecular species, including salts, are selectively transferred from the solution to the solvent against the osmotic current with a selectivity greater than the ratio of the relative diffusion coefficients of the separated species; and
(ii) subsequently subjecting said solution to ultrafiltration with a semipermeable membrane,
permitting the passage therethrough of water or other solvent component of said solution, together with sugar molecules contained therein, to form a permeate of treated product containing said sugar molecules, and
preventing the passage of macro-molecular species, such as protein, contained in said solution to form a concentrate or retentate thereof.

18. The process according to claim 17, wherein said sugar-containing solution is molasses.

19. The process according to claim 17, wherein said sugar-containing solution is molasses distillation residues or dunder.

20. Apparatus for the fractionation of a primary liquid containing a plurality of dissolved molecular species of different molecular weights, comprising:
(i) a diffusion barrier for selective counter diffusion comprising a microporous matrix having one or more insoluble inorganic salts in the pores of the matrix and on the surfaces at one side of the matrix and forming an immobilized inorganic molecular grid or screen having a substantially uniform lattice structure defining pores or channels therethrough in the range of from about 10 Angstroms to about 50 Angstroms in diameter, thus providing a diffusion barrier means having a substantially uniform matrix permeability to enhance selectivity which is used to separate said primary liquid from a second liquid in a fractionation process whereby small molecular species may diffuse through the diffusion barrier against an osmotic current existing between said primary liquid and said second liquid, from said primary liquid to said second liquid under the influence of an osmotic gradient between the primary and second liquids to provide a selectivity greater than the ratio of the relative diffusion coefficients of the separated species; and
(ii) ultrafiltration means whereby said primary liquid may subsequently be selectively split into a permeate of a product containing solvent and molecules below a predetermined size, and a concentrate or retentate comprising molecules above said predetermined size.

21. The apparatus according to claim 20, wherein said diffusion barrier means comprises one or more hollow fibre tube units, each comprising a tubular housing; a bundle of porous hollow fibres arranged within the housing in the axial direction thereof; a countercurrent liquid chamber formed between the outer surfaces of the hollow fibre bundle and the inner surface of the housing; first inlet and outlet ports for passing the second liquid into and out of said liquid chamber; partition walls supporting the hollow fibre bundle, separating the open ends of the hollow fibres from the liquid chamber and defining the length of the liquid chamber; and second inlet and outlet ports for the primary liquid phase, said second inlet and outlet ports communicating with the interior space or lumen of each of the hollow fibres, and wherein a plurality of pores or channels of predetermined molecular dimensions and permeability communicate between the interior space or lumen of each hollow fibre and said liquid chamber.

22. The apparatus according to claim 21, wherein the first inlet and outlet ports of each hollow fibre tube unit are connected in series to the first inlet and outlet ports of a second hollow fibre tube unit for circulation of said second liquid therebetween.

23. The apparatus according to claim 22, wherein means are provided for directing at least part of the treated second liquid back to the stream of primary liquid to be treated by said apparatus, and wherein further means are provided to add pure second liquid to replace the treated second liquid which has been removed.

24. The apparatus according to claim 23, wherein ion exchange means or other means capable of fixing by adsorption is provided to remove compounds from the second liquid which have diffused therein from the primary liquid.

25. A process for the separation by counter diffusion of small molecular species from a primary fluid containing a plurality of molecular species of different molecular weights, comprising:
  subjecting said primary fluid to treatment with a diffusion barrier for selective counter diffusion which separates the primary fluid from a second fluid, the primary fluid and second fluid being such that an osmotic gradient exists between the primary fluid and the second fluid and causes osmotic current to flow from said second fluid through said barrier to said primary fluid, and including the step of adjusting one of the shear rate of the primary fluid along one side of the barrier and the osmotic gradient across the barrier whereby small molecular species are selectively transferred from the primary fluid to the second fluid against the osmotic current with a selectivity greater than the ratio of the relative diffusion coefficient of the separated species, and said diffusion barrier comprising a microporous matrix having one or more insoluble inorganic salts in the pores of the matrix and onto the surfaces at the said one side thereof to form an immobilized inorganic molecular grid or screen having a substantially uniform lattice structure and substantially uniform matrix permeability.

26. A process according to claim 25, wherein:
  said diffusion barrier comprises a hollow fibre tube unit, and wherein the primary fluid is circulated through the inner channels or lumens of a bundle of hollow fibres, whereby the small molecular species can diffuse through the uniform molecular grid matrix structure in the walls of the hollow fibres and be separated from the primary fluid.

27. Apparatus for the fractionation of a primary liquid containing a plurality of dissolved molecular species of different molecular weights, comprising:
  a diffusion barrier for selective counter diffusion comprising a microporous matrix having one or more insoluble inorganic salts in the pores of the matrix and onto the surfaces at one side thereof to form an immobilized inorganic molecular grid or screen having a substantially uniform, lattice structure defining pores or channels in the range of from about 10 Angstroms to about 50 Angstroms in diameter, thus providing a diffusion barrier means having a substantially uniform matrix permeability to enhance selectivity, and which is used in a fractionation process to separate said primary liquid from a second liquid whereby small molecular species may diffuse through the diffusion barrier, against an osmotic current existing between said primary and second liquids, from said primary liquid to said second liquid under the influence of an osmotic gradient between the primary and second liquid, to provide a selectivity greater than the ratio of the relative diffusion coefficients of the separated species.

28. Apparatus according to claim 27, wherein:
  said diffusion barrier comprises one or more hollow fibre tube units, each comprising a tubular housing; a bundle of porous hollow fibres arranged within the housing in the axial direction thereof; a counter current liquid chamber formed between the outer surfaces of the hollow fibre bundle and the inner surface of the housing; first inlet and outlet ports for passing the second liquid into and out of the said liquid chamber; partition walls supporting the hollow fibre bundle, separating the open ends of the hollow fibres from the liquid chamber and defining the length of the liquid chamber; and second inlet and outlet ports for the primary liquid phase, said second inlet and outlet ports communicating with the interior space or lumen of each of the hollow fibres, and wherein a plurality of pores or channels of predetermined molecular dimensions and permeability communicate between the interior space or lumen of each hollow fibre and said liquid chamber.

29. Apparatus according to claim 28, wherein the first inlet and outlet ports of each hollow fibre tube unit are connected in series to the first inlet and outlet port of a second hollow fibre tube unit for circulation of said second liquid therebetween.

30. Apparatus according to claim 29, wherein means are provided for directing at least part of the treated second liquid back to the stream of primary liquid to be treated by said apparatus, and wherein further means are provided to add pure second liquid to replace the treated second liquid which has been removed.

31. Apparatus according to claim 28, wherein:
  ion exchange means or other means capable of fixing by adsorption is provided to remove compounds from the second liquid which have diffused therein from the primary liquid.

32. A process for the separation by counter diffusion of small molecular species from a primary liquid containing a plurality of dissolved molecular species of different molecular weights, said process comprising the steps of:
  providing a diffusion barrier comprising a microporous matrix having one or more insoluble inorganic salts in the pores of the matrix and forming a substantially uniform structure defining pores or channels therethrough having a diameter in the range of about 10 to about 50 Angstroms;
  providing said primary liquid on one side of said diffusion barrier;
  providing on the other side of said diffusion barrier a solvent having a lower osmotic pressure than the primary liquid, such that an osmotic gradient exists between said solvent and said primary liquid and causes osmotic current to flow from said other side of said diffusion barrier through said diffusion barrier to said one side thereof;
  causing said primary liquid to flow along said one side of said diffusion barrier in a direction generally parallel to said one side thereof; and,
  adjusting at least one of the shear rate of said primary liquid along said one side of said diffusion barrier and said osmotic pressure gradient across said diffusion barrier such that said molecular species are selectively transferred from said primary liquid to said solvent through said barrier against said osmotic gradient and current with a selectivity greater than the ratio of the relative diffusion coefficients of the separated species.

33. The process according to claim 32, wherein the diffusion barrier comprises a hollow fibre tube unit, wherein the primary liquid is circulated through the inner channels or lumens of a bundle of hollow fibres and wherein the solvent is circulated in the space surrounding the bundle of hollow fibres, whereby the one other of said small molecular species can diffuse through the uniform molecular grid matrix structure in the walls of the hollow fibres against the osmotic current and into the solvent.

34. The process according to claim 33, wherein the solvent circulating in the space surrounding the bundle of fibres is further treated in a cascade system to separate the molecular species contained therein.

35. The process according to claim 34, wherein the solvent circulating in the space surrounding the bundle of hollow fibres is circulated to the space surrounding the bundle of hollow fibres of a second hollow fibre tube unit wherein an osmotic gradient exists between the solvent in said space and a further solvent circulating through the interior channels or lumens of the hollow fibres of said second hollow fibre tube unit whereby small molecular species are selectively transferred from the solvent in said space to the further solvent circulating through the interior channels or lumens of the hollow fibres of said second hollow fibre tube unit.

36. The process according to claim 35, wherein the treated solvent from the space surrounding the bundle of hollow fibres of said second hollow fibre tube unit is circulated back to the space surrounding the bundle of hollow fibres of the first hollow fibre tube unit.

37. The process according to claim 36, wherein a part of the treated solvent from the space surrounding the bundle of hollow fibres of said second hollow fibre tube unit is circulated back to the stream of primary liquid to be treated by the first hollow fibre tube unit.

38. The process according to claim 37, wherein pure solvent is added to the circulating solvent stream to replace the volume of solvent which has been circulated back to the stream of primary liquid to be treated.

39. A diffusion barrier for selective counter diffusion, comprising a microporous matrix including a plurality of porous hollow fibre membranes each having a wall thickness of not more than about 15 microns and having one or more inorganic salts in the pores and on the inside surfaces of the cores of the hollow fibre membranes to form an immobilized grid or screen having a substantially uniform lattice structure defining pores or channels through the walls of the fibre membranes having a diameter in the range of from about 10 Angstroms to about 50 Angstroms and providing said diffusion barrier with substantially uniform permeability.

40. A diffusion barrier for selective counter diffusion, comprising a microporous matrix having one or more inorganic salts deposited in the pores and on the surfaces at one side of the matrix to form an immobilized grid or screen having a substantially uniform lattice structure defining pores or channels through the matrix having a diameter in the range of about 10 to about 50 Angstroms, said diffusion barrier having substantially uniform permeability.

* * * * *